United States Patent [19]

Hayakawa et al.

[11] Patent Number: 4,584,086

[45] Date of Patent: Apr. 22, 1986

[54] DEVICE FOR DETECTING CONCENTRATION OF OXYGEN IN EXHAUST GAS

[75] Inventors: Nobuhiro Hayakawa; Masahiko Yamada; Toshiyuki Ishihara, all of Aichi, Japan

[73] Assignee: NGK Spark Plug Co., Ltd., Aichi, Japan

[21] Appl. No.: 723,979

[22] Filed: Apr. 16, 1985

[30] Foreign Application Priority Data

Apr. 16, 1984 [JP] Japan .................................. 59-77328

[51] Int. Cl.$^4$ ............................................. G01N 27/58
[52] U.S. Cl. .................................. 204/429; 427/125; 427/126.3
[58] Field of Search .............. 204/429, 424, 425, 426, 204/1 S; 427/125, 126.3

[56] References Cited

U.S. PATENT DOCUMENTS

| | | | |
|---|---|---|---|
| 3,935,089 | 1/1976 | Togawa et al. | 204/429 |
| 3,978,006 | 8/1976 | Topp et al. | 204/429 X |
| 4,021,326 | 5/1977 | Pollner et al. | 204/429 |
| 4,199,425 | 4/1980 | Sinkevitch | 204/429 |
| 4,272,349 | 6/1981 | Furutani et al. | 204/429 |
| 4,476,008 | 10/1984 | Sano et al. | 204/425 |

FOREIGN PATENT DOCUMENTS 41794 4/1979 Japan .................................. 204/429

Primary Examiner—G. L. Kaplan
Attorney, Agent, or Firm—Sughrue, Mion, Zinn, Macpeak and Seas

[57] ABSTRACT

A device for detecting the concentration of oxygen in an automotive exhaust gas, particularly, an automotive exhaust gas containing lead, providing reliable operation for long operating periods. The device includes an oxygen-ion-conductive solid electrolyte positioned between the atmosphere and the gas to be measured, and electrodes made of an electroconductive material, one of which is located on the surface of the solid electrolyte contacted by the atmosphere and the other on the surface of the electrolyte contacted by the exhaust gas. The surface of the electrode in contact with the exhaust gas is coated with a protective, heat-resistive metal oxide layer having supported thereon a uniform layer of a lead-trapping thermally stable metal in a molar amount of 0.4% of the metal oxide.

2 Claims, 6 Drawing Figures

DEVICE FOR DETECTING CONCENTRATION OF OXYGEN IN EXHAUST GAS

BACKGROUND OF THE INVENTION

The present invention relates to a device for detecting the concentration of oxygen in automotive exhaust gas. More particularly, the invention relates to a device for detecting the concentration of oxygen in a lead-containing exhaust gas.

A conventional device for detecting the concentration of oxygen in automotive exhaust gases is shown in partial cross section in FIG. 1. The device includes four components: an oxygen-ion-conductive solid electrolyte 1, electrodes 2 and 3 made of an electroconductive material, and a protective layer 4. The solid electrolyte 1 is positioned between the atmosphere A and the exhaust gas or emission E and generates an electromotive force in proportion to the differential oxygen concentration between the atmosphere and the exhaust gas. The electrode 2 is positioned on the inner surface of the solid electrolyte 1 with the electrode 3 on its outer surface. Both electrodes act as oxidation catalysts. The protective layer 4 is used to protect the electrode 2 from the physical and chemically corrosive effects of the exhaust gas.

Two examples of such a conventional device are disclosed in Japanese Unexamined Published Patent Applications Nos. 89686/1979 and 13828/1980. The devices described in these documents use a double- or triple-layered structure for the protective layer 4. However, because of the relative thinness of this protective layer 4 (typically less than about 100 microns), lead cannot be trapped in a sufficient amount to provide the desired resistance to lead contamination.

Japanese Unexamined Published Patent Applications Nos. 90294/1973 and 53456/1981 disclose other examples of conventional oxygen detectors. In order to provide an enhanced resistance to lead contamination, the protective layer 4 used in these examples is deposited with a lead-trapping metal through dipping process. However, depending on the dipping method employed, the lead-entrapping metal is mostly supported on the outer surface of the protective layer 4 and lead has a tendency to be deposited only in that area, thus causing occasional clogging that may eventually lead to a lowered responsiveness of the detector. The protective layer 4 is also equipped with a lead-resistant catalyst layer, but if the concentration of the catalyst is increased with a view to enhancing the resistance to lead contamination, the responsiveness of the detector is decreased. A lowered responsiveness is also caused by using an excessively thick catalyst layer.

Japanese Patent Publication No. 18146/1982 discloses a detector that employs an electrode coated with a protective layer 4 which is formed by first applying a slip containing a heat-resistive metal oxide and a catalytic material, drying the slip, and then sintering the dried slip. The biggest problem with this type of detector lies in the fact that it is difficult to prepare a slip having an optimum porosity. An excessively small porosity will prevent the entrance of gases into the detector, and if the porosity is too great, the protective layer 4 may be corroded by a reducing exhaust gas, possibly resulting in an open-circuit failure in the electrode 2. Additionally, the slip has a tendency to not firmly adhere to the electrode 2 and may easily come off during service.

SUMMARY OF THE INVENTION

A primary object, therefore, of the present invention is to provide a device for detecting the concentration of oxygen in automotive exhaust gas that is not only durable but also capable of detecting the oxygen concentration of the exhaust gas with an improved response by preventing lead from poisoning the sensing electrodes, clogging the protective layer and building up on the under-surface of the protective layer.

The present invention has been accomplished in order to attain the objects shown above. The invention provides a device for detecting the concentration of oxygen in automotive exhaust gas including an oxygen-ion-conductive solid electrolyte positioned between a reference gas and a gas of which the oxygen concentration is to be measured, which electrolyte generates an electromotive force proportional to the difference in oxygen concentration between the two gases, and electrodes made of an electroconductive material, one located on the surface of the oxygen-ion-conductive solid electrolyte contacted by the reference gas and the other located on the surface of the solid electrolyte contacted by the gas to be meausred, wherein the surface of the electrode in contact with the gas to be measured is coated with a protective, heat-resistive metal oxide layer having supported thereon uniformly a lead-trapping thermally stable metal, the lead-trapping metal being present in a molar amount of 0.4 to 3% of the metal oxide.

DESCRIPTION OF THE PREFERRED EMBODIMENTS

A preferred embodiment of a detector of the present invention will hereunder be described with reference to FIGS. 2 to 6.

Figure 1:
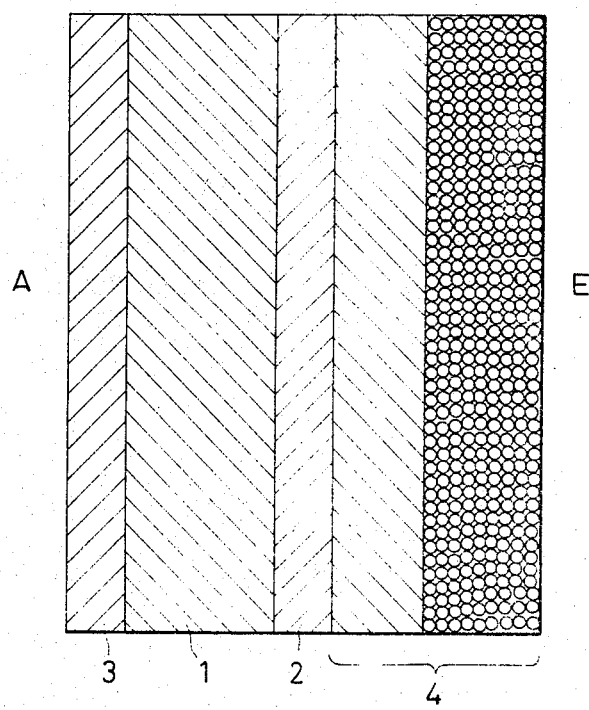
FIG. 1 shows a partial cross section of a conventional device for detecting the concentration of oxygen in automotive exhaust.
Figure 2:
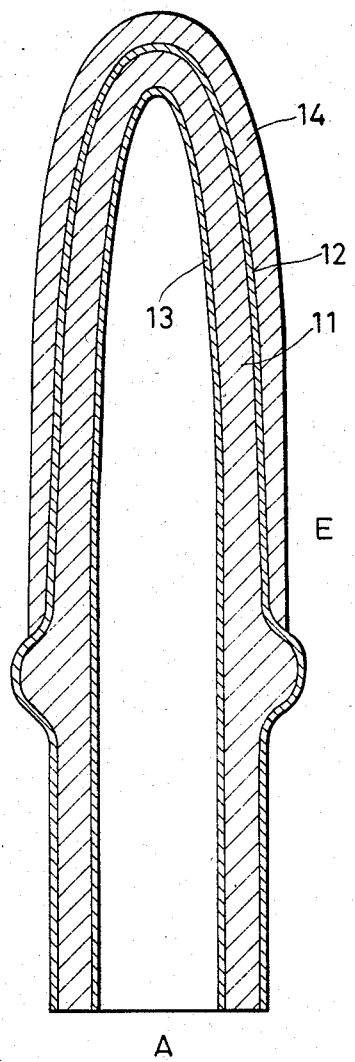
FIG. 2 is a cross section of an oxygen sensor in accordance with a preferred embodiment of the present invention.

FIG. 2 shows an oxygen concentration detector constructed in accordance with a preferred embodiment of the present invention. The detector includes an oxygen-ion-conductive solid electrolyte 11 made of an oxygen-ion-conductive metal oxide such as $ZrO_2$ stabilized with, for example, $Y_2O_3$. This electrolyte may be prepared by grinding a mix, calcining with the particles of the mix, compacting the calcined particles into a suitable sheath form, and firing the compact at elevated temperatures to provide a dense sinter. The outer surface of the solid electrolyte 11 is coated with a first electrode 12, typically made of platinum, provided by chemical plating, vapor deposition, sputtering or paste application. The inner surface of the solid electrolyte 11 is provided with a second electrode 13. The electrode 12 is overlaid with a homogeneous protective layer 14 made from an $Al_2O_3 \cdot MgO$ spinel powder and a lead-trapping metal such as Pt, Ru, Pd, Ni, Au, or alloys thereof.

The protective layer 14 is preferably made by the following steps: providing a metal oxide mix ($Al_2O_3$.-MgO spinel), grinding, sieving (+25 microns, −63 microns), chemical plating of Pb getter metal (Pt) to the metal oxide powder, drying, and plasma spraying. Platinum is chemically plated to the metal oxide powder by the steps of: preliminarily treating the metal oxide, nucleating the Pb getter, and chemically plating a Pb getter such as by precipitating a Pb getter metal on the surfaces of the metal oxide particles from a solution containing a predetermined weight of the getter metal.

The protective layer thus formed may be subjected to a heat treatment in a hydrogen furnace at between 600° and 700° C. Instead of chemical plating, vapor deposition techniques may be employed to form a Pt layer on the metal oxide particles. The oxygen-ion-conductive solid electrolyte 11, first electrode 12, second electrode 13, and protective layer 14 constitute the device of the present invention for detecting the concentration of oxygen in automotive exhaust gas. The detector is mounted on the inner wall of the exhaust system, equipped with a protective cover (not shown), and mounted at a position in such a predetermined manner that it forms a wall between the exhaust gas and the atmosphere. With this arrangement, the exhaust gas E flows on the surface of the protective layer 14, whereas atmospheric air A enters the detector from the bottom so as to make contact with the second electrode 13.

The mechanism by which the detector of the present invention operates is as follows: First, the gradient of oxygen concentration between the atmosphere and the exhasut gas forces the oxygen molecules in the atmosphere to enter the second electrode 13 where they are ionized. Then, the oxygen ions pass through the solid electrolyte 11 to reach the first electrode 12 where most of them are converted to molecular form, thereby producing an electromotive force. During this process, the exhaust gas around the first electrode 12 will remain in chemical equilibrium so long as that electrode ensures a proper catalytic effect.

Figure 3:
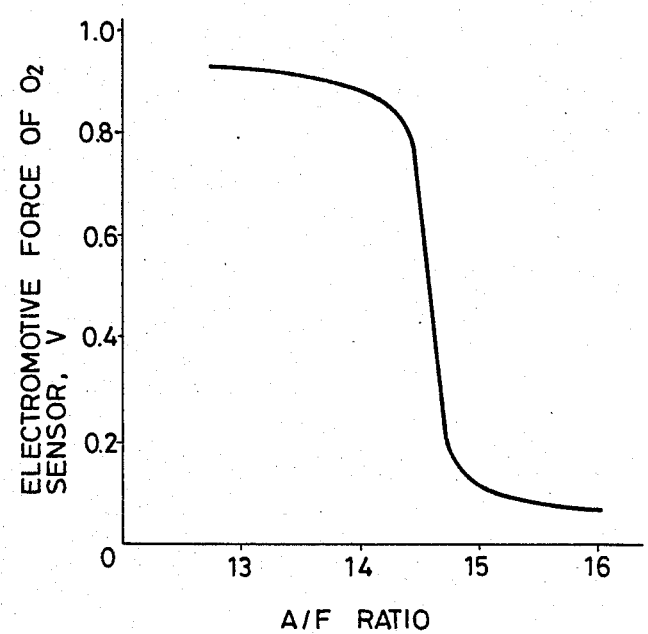
FIG. 3 is a graph showing the relationship between the A/F (air/fuel) ratio and electromotive force generated by the sensor of FIG. 2.
Figure 4:
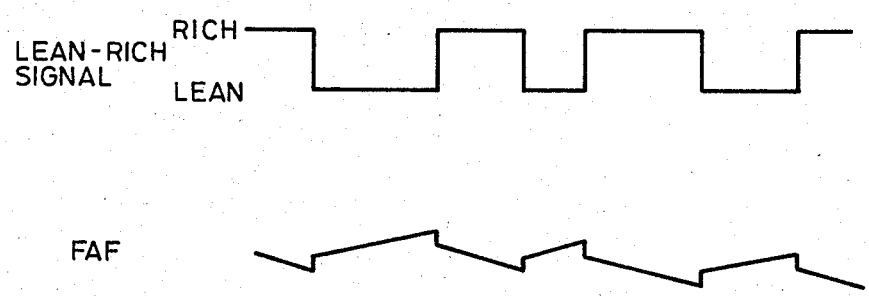
FIG. 4 shows the waveform of a lean-rich signal produced by the sensor of FIG. 2 and the waveform of a feedback correction factor FAF obtained by integrating such lean-rich signal.

The relationship between the A/F ratio and the electromotive force generated by the differential oxygen partial pressure at the two electrodes is shown by the graph of FIG. 3. This characteristic curve is Z shaped, and the EMF makes an abrupt change at a point about the theoretical A/F ratio.

In an A/F ratio control system using the detector described above, the detector senses the concentration of residual oxygen in the exhaust gas, and the data obtained therefrom is used to estimate the A/F ratio of the air intake system, whereby the engine may be made to operate at the theoretical A/F ratio. The A/F ratio of the intake system may be adjusted to a point around the theoretical value by the following procedure: calculating the basic injection time $t_p$ based on the amount of air intake Q and the engine speed (rpm), obtaining the A/F ratio feedback correction factor FAF by performing an integral operation on the lean-rich signal from the detector using a feedback integral constant; multiplying $t_p$ by FAF to determine the fuel injection time TAU; and performing ON/OFF control on the fuel injection valve so that it remains open for the period of fuel injection time TAU.

Figure 5:
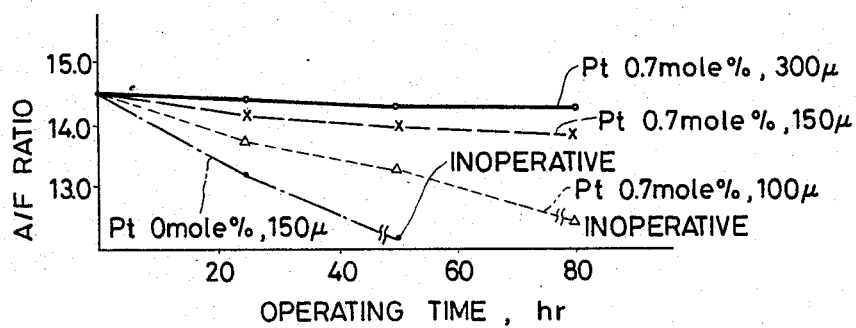
FIG. 5 is a graph showing the time vs. A/F ratio of the sensor of FIG. 2 with the thickness of the protective layer taken as a parameter.

Tests were conducted to measure the concentration of oxygen in a lead-containing exhaust gas with the detector of the present invention used in an engine running on gasoline containing 1.5 g of Pb per gallon. FIG. 5 shows the relationship between the operating time of this sensor and the A/F ratio measured for the actual emissions. In this test, four detector samples were used; the first three used protective layers 14 that contained 0.7 mol% of Pt as a Pb getter and which had thicknesses of 100 microns, 150 microns and 300 microns, while the protective layer of the fourth sample contained no Pt and had a thickness of 150 microns. In the second sample with a thickness of 100 microns, Pb was not very efficiently trapped by Pt and penetrated through the protective layer to poison the first electrode 12. The deteriorated first electrode no longer had the ability to rapidly absorb oxygen molecules in the exhaust gas. The catalytic action of the first electrode 12 was thus impaired and the HC and CO components in the exhaust gas were very slowly oxidized with the oxygen molecules at the electrode 12. As a result, the lean-rich signal shown in FIG. 2 shifted toward the rich side, causing a change in the A/F ratio feedback correction factor FAF and a subsequent increase in the fuel injection time TAU. The detected A/F ratio gradually shifted to the rich side and the detector eventually became inoperative, as indicated in FIG. 5. A protective layer thicker than 500 microns did not permit sufficiently rapid penetration of the exhaust gas and decreased the initial response of the sensor. It is therefore concluded that the thickness of the protective layer 14 preferably ranges from 150 microns to 500 microns.

Figure 6:
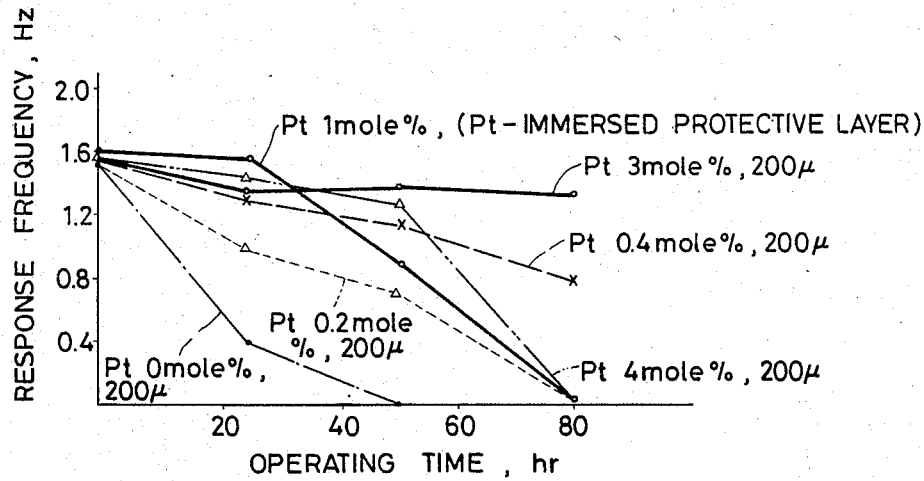
FIG. 6 is a graph showing the time vs. response frequency of the sensor of FIG. 2 with the content of the Pb getter (Pt) taken as a parameter.

FIG. 6 shows the relationship between the operating time of the $O_2$ sensor and the frequency response of the lean-rich signal from the sensor. The good response of the sensor is represented by a high response frequency. The data in FIG. 6 assumes a constant film thickness (200 microns) with the Pt content of the protective layer ranging from 0 to 4 mol%. The response frequency of the samples using protective layers with Pt levels outside the range of 0.4 to 3 mol% decreased with operating time, and the rate of decrease was accelerated as the operating time exceeded 50 hours. The samples using protective layers containing 0.2 mol% and 4 mol% of Pt became substantially insensitive when the operating time exceeded 80 hours. A protective layer with very small Pt content is unable to prevent poisoning of the first electrode by lead. A protective layer with excessive pt is also undesirable since the gradual buildup of Pb on the surface prevents the smooth flow of the exhaust gas and adversely affects the response time of the sensor.

FIG. 6 also shows data for a detector sample using a protective layer having 1 mol% of Pt deposited in the outer surface. The Pt content of the layer was within the preferred range of 0.4 to 3 mol%, but the unevenness in the Pt concentration that inevitably resulted from the dipping technique increased the likelihood of Pb buildup on the outer surface of the protective layer or its being clogged with Pb. As a result, the response of the sensor started to deteriorate when the operating time exceeded 20 hours, and no response was obtained after 80 hours. Sensors using protective layers of Pt levels in the range of 0.4 to 3 mol% prepared in accordance with the present invention produced satisfactory results, although their response decreased slightly with operating time. It is therefore concluded that the preferred range of the content of a Pb getter (Pt in the embodiment shown) in the protective layer 14 is from 0.4 to 3 mol%. Substantially the same results were obtained with protective layers having thicknesses other than 200 microns, except that the initial value of the response frequency had a tendency to decrease with thicker layers. The initial value of the response frequency is preferably not lower than 0.7 Hz.

An oxygen sensor produced in accordance with the preferred embodiment of the present invention which uses a protective layer 14 of a thickness of 150 to 500 microns and which has a Pt content of 0.4 to 3 mol% may be used for the purposes of efficient purification of a lead-containing car exhaust gas. This can be achieved by performing feedback control on the internal combustion engine so that it is operated at the theoretical A/F ratio as determined by the electromotive force of the sensor.

As described above, in accordance with the preferred embodiment of the present invention, not only can Pb poisoning of the first electrode 12 be prevented, but also clogging of the protective layer 14 with Pb or its deposition on the outer surface of that layer is effectively suppressed. Because of these features, the sensor of the present invention is capable of precise measurement of the concentration of oxygen in exhaust gas with a good response time. Additionally, the sensor can be operated reliably over extended periods.

In the embodiment shown above, Pt is used as the Pb getter. Other suitable Pt-trapping materials include Ru, Pd, Ni, Au, Ag, Ir, Os, $Ni/Ni_2$, $SiO_2$, Ni/cr, BaO, CuO/Cr, and $SrO_2$. The protective layer 14 may be made of materials other than $Al_2O_3.Y_2O_3$, including CaO, $ZrO_2$, $Y_2O_3.ZrO_2$, and $Al_2O_3.BeO$.

Thus, the present invention provides a device for detecting the concentration of oxygen in automotive car exhaust gas including a oxygen-ion-conductive solid electrolyte positioned between a reference gas and a gas to be measured, which electrolyte generates an electromotive force proportional to the differential oxygen concentration between the two gases, and electrodes made of an electroconductive material, one located on the surface of said oxygen-ion-conductive solid electrolyte contacted by the reference gas and the other located on the surface of the solid electrolyte contacted by the gas to be measured. In accordance with the invention, the surface of the electrode in contact with the gas to be measured is coated with a protective, heat-resistive metal oxide layer having supported thereon a uniform layer of a lead-trapping thermally stable metal, the lead-trapping metal being present in a molar amount of 0.4 to 3% of the metal oxide.

The sensor of the present invention is free not only from poisoning of the inner electrode, but also from clogging of the protective layer with Pb and its buildup on the outer surface of the protective layer. As a result, the sensor ensures accurate measurement of the oxygen concentration of exhaust gas with a good response time maintained over prolonged periods of service.

While the oxygen sensor of the present invention has been described above by reference to a preferred embodiment, it should be understood that the scope of the invention is by no means limited to that particular embodiment and various modifications may be made without departing from the spirit and scope of the invention.

We claim:

1. A device for detecting the concentration of oxygen in an automotive exhaust gas, comprising: an oxygen-ion-conductive solid electrolyte positioned between a reference gas and a gas to be measured, said electrolyte generating an electromotive force proportional to a differential oxygen concentration between the two gases, and electrodes made of an electroconductive material, a first one of said electrodes being located on a surface of said oxygen-ion-conductive solid electrolyte contacted by said reference gas and a second one of said electrodes being located on a surface of said solid electrolyte contacted by said gas to be measured, said surface of said electrode in contact with said gas to be measured being coated with a protective, heat-resistive metal oxide layer having supported thereon uniformly a lead-trapping, thermally stable metal, said lead-trapping metal being present in a molar amount of 0.4 to 3% of said metal oxide, wherein:

said protective layer is formed by first chemically plating or evaporating said lead-trapping metal onto said heat-resistive metal oxide powder(s), and then plasma spraying the thus-treated metal oxide powder(s) onto the second electrode, and wherein said protective layer has a thickness in a range of 150 to 500 microns.

2. The device according to claim 1, wherein said lead-trapping metal is selected from the group consisting of Pt, Ru, Pd, Ni, Au, and alloys thereof.

* * * * *